United States Patent [19]

Makishita et al.

[11] Patent Number: 5,453,699
[45] Date of Patent: Sep. 26, 1995

[54] TAB TESTER FOR RECOGNIZING IMAGE OF TAB

[75] Inventors: Hiroyuki Makishita; Yukiyasu Takano; Toshiyuki Tezuka; Yasuhisa Kitajima, all of Tokyo, Japan

[73] Assignee: Ando Electric Co., Ltd., Tokyo, Japan

[21] Appl. No.: 290,486

[22] Filed: Aug. 15, 1994

[30] Foreign Application Priority Data

Sep. 17, 1993 [JP] Japan .................................. 5-254806

[51] Int. Cl.⁶ .................................................. G01N 21/89
[52] U.S. Cl. ........................ 324/754; 324/158.1; 324/765; 348/126
[58] Field of Search ................................ 324/158.1, 754, 324/752, 755, 73.1, 765; 437/8, 220; 439/482; 348/126; 356/394; 29/827

[56] References Cited

U.S. PATENT DOCUMENTS

| | | | |
|---|---|---|---|
| 4,980,219 | 12/1990 | Hiraide et al. | 428/134 |
| 5,019,209 | 5/1981 | Hiraide et al. | 29/827 |
| 5,059,559 | 10/1991 | Takahashi et al. | 437/220 |
| 5,331,397 | 7/1994 | Yamanaka et al. | 348/126 |

*Primary Examiner*—Vinh P. Nguyen
*Attorney, Agent, or Firm*—Flynn, Thiel, Boutell & Tanis

[57] ABSTRACT

A TAB tester for recognizing image on or before testing the TAB so as to prevent erroneous detection. There are provided first, second and third image cameras. The second image camera is disposed upstream relative to a first sprocket, namely, at the front stage of measurement of a tape carrier and it takes a second image of the TAB and outputs a second image to an image processing unit. The third image camera is disposed downstream relative to a punch unit, namely, at the rear stage of the measurement of the tape carrier and it takes a third image of the TAB and outputs the third image to the image processing unit. The image processing unit converts the second and third images into second and third processed image data. The second processed image data is supplied to a control unit where it is stored as data of necessity of measurement of the TAB. The third processed image data is supplied to the control unit where the third processed image data is compared and collated with the second processed image data and a punching result by the punching unit.

2 Claims, 4 Drawing Sheets

TAB TESTER FOR RECOGNIZING IMAGE OF TAB

BACKGROUND OF THE INVENTION

1. Field of the Invention

The present invention relates to a TAB (tape automated bonding) tester for recognizing a state of the TAB by an image before it is measured or after it is measured and classified.

2. Prior Art

An arrangement of a prior art TAB tester will be described with reference to FIG. 4. The TAB tester comprises a supply reel 2 on which a tape carrier 11 is mounted or wound, a pusher 4 for pushing down the tape carrier 11 downward for permitting the tape carrier 11 to contact an IC tester so as to conduct the TAB so that the TAB is subjected to an electric test by the IC tester, sprockets 5A and 5B which are synchronously rotated for transferring the tape carrier 11, a group of detectors 12 for detecting the TAB to judge that it is a reader tape or the TAB to be tested, a punch unit 6 for punching the TAB of the tape carrier 11 depending on the result of electric test of the TAB by the IC tester to form an identification hole or punching an IC chip, a group of detectors 13 for detecting data and an accommodating or winding reel 3 for accommodating or winding the tape cartier 11 which was subjected to the electric test.

There are also provided an image camera 7A for taking an image of the TAB with the help of light emitted from a light source 8A, an image processing unit 9 for receiving and processing the image taken by the image camera 7A to thereby convert the image into an image data, a control unit 10 for receiving the image data from the image processing unit 9 and controlling the position of the TAB when the TAB is measured.

The group of detectors 12 comprise three detectors and they are disposed upstream relative to the sprocket 5A. The group of detectors 13 comprise three detectors and they are disposed downstream relative to the sprocket 5A. The arrangement of the group of detectors 12 is the same as that of the group of detectors 13.

FIG. 5 is an arrangement of the group of detectors 12. A detector body 20 is formed of a U-shape and comprises a light emitter 21 at the first tip end thereof and a light receiver 22 at the second tip end thereof at the portion confronting the light emitter 21.

In FIG. 5, the tape carrier 11 travels on the groove defined in the detector body 20 so as to detect the TAB. The detector body 20 is held by a moving body 23 and moves forward and backward relative to the traveling direction of the tape carrier 11 in the direction to traverse the traveling direction. The moving body 23 moves in parallel with the traveling direction of the tape carrier 11. The groups of the detectors 12 and 13 have the arrangements as illustrated in FIG. 5 and the detecting positions thereof are adjusted before the TAB tester operates.

The group of the detectors 12 comprises detectors 12A, 12B and 12C which are disposed on the tape carrier 11 as illustrated in FIG. 6. In FIG. 6, the detector 12A is adjusted to be positioned at the portion where the detecting light shields one of test pads 11A. The detector 12B is adjusted to be positioned at the portion where the detecting light shields the IC chip 11B. The detector 12C is adjusted to be positioned at the portion where the detecting light transmits a marked hole 11C. The detector 12A confirms that the tape cartier 11 is a reader tape or the TAB to be tested based on the presence of the detecting light. The detector 12B confirms the presence or nonpresence of the IC chip 11B based on the presence or the nonpresence of the detecting light, thereby judging the necessity of the measurement of the TAB. The detector 12C confirms the presence or nonpresence of the marked hole 11C based on the presence or nonpresence of the detecting light and also confirms that the TAB has been already measured and classified.

Depending on various testing steps of the TAB, the marked hole 11C on the TAB is used for testing again the TAB on which the marked hole 11C is punched or punching an identification hole by the punch unit 6 showing better or poor goods after the TAB is tested.

An operation of the conventional TAB tester as shown in FIG. 4 will be described hereinafter.

Data of TAB detected by the group of detectors 12 is stored in the control unit 10. When the detected TAB is moved under the pusher 4, the control unit 10 reads the data of TAB and issues instruction of necessity of the measurement of the TAB by the IC tester.

The TAB which is instructed to be measured by the control unit 10 is positioned to an electrode, not shown, connected to the IC tester and subjected to an electric test. After the TAB was subjected to the electric test, it moves to the punch unit 6. The punch unit 6 punches the identification marked hole 11C or punches the IC chip 11B.

Successively, when the TAB moves to the group of detectors 13, the data stored in the group of detectors 12 and the result of classification by the punch unit 6 are compared and collated with the data detected by the group of detectors 13. If the result of comparison and collation shows that both the data are agreed with each other, the tape carrier 11 is unwound on or accommodated in the accommodating reel 3. When the group of detectors 13 detect the tape carrier 11 which was completely wound, they judge that the tape carrier 11 is the tape end and a series of operations complete.

Depending on various testing steps, the TAB is tested by a burn-in tester in the step before it is tested by the TAB tester in FIG. 4. When the TAB is tested by the burn-in tester, the tape carrier 11 is cut in a given length. Accordingly, in the step where the TAB is tested by the TAB tester, the tape carrier 11 is moved while a TAB 11D and a TAB 11E are connected to each other by an adhesive tape as shown in FIG. 6.

In the TAB tester in FIG. 4, if there are joints on the tape carrier 11 as shown in FIG. 6, there is a possibility that the TAB is erroneously detected since the TAB is not transferred accurately to the setting position of each sensor unit. In addition, there is a possibility that the TAB is not measured since the detecting means 1 of FIG. 6 judges that there is no IC chip because the IC chip has been recently miniaturized in the width of e.g. about 1 mm.

SUMMARY OF THE INVENTION

It is an object of the present invention to provide a TAB tester having a second image camera disposed upstream relative to a first sprocket and a third image camera disposed downstream relative to a punch unit wherein necessity of measurement is judged by a second image camera and image taken by the second image camera and result of punching by a punch unit are compared and collated width data taken by a third image camera.

To achieve the above object, the TAB tester according to the present invention comprises a supply reel 2 on which a tape carrier 11 is mounted, a pusher 4 for pushing down the tape carrier 11 downward for permitting the tape carrier 11 to contact an IC tester so that the TAB can be subjected to an electric test by the IC tester, a punch unit 6 for punching the TAB of the tape carrier 11 depending on the result of electric test by the IC tester to form an identification hole or punching an IC chip, first and second sprockets 5A and 5B which are synchronously rotated for transferring the tape carrier 11, a first image camera 7A disposed under the pusher 4 for taking a first image of the TAB which is transmitted by a light source 8A and outputting the first image as a first image data, a second image camera 7B disposed upstream relative to the first sprocket 5A, the second image camera 7B taking a second image of the TAB and outputting the second image as a second image data, a third image camera 7C disposed downstream relative to the punch unit 6, the third image camera 7C taking a third image of the TAB and outputting the third image as a third image data. The TAB tester further comprises an image processing unit 9 for receiving first, second and third images from the first, second and third image cameras 7A, 7B and 7C and subjecting the first, second and third images to image processings, a control unit 10 for controlling the position of the TAB based on the first processed image data when the TAB is measured, instructing execution and non-execution of the measurement of the TAB based on the second processed image data, and comparing and collating the third processed image data with the second processed image data and the punching result by the punch unit 6 upon reception of the first, second and third processed image data from the image processing unit 9, and a winding reel 3 for winding the tape carrier 11 therein which was subjected to an electric test.

According to the present invention, the second image camera 7B is disposed at the portion where the group of detectors 12 of the conventional TAB tester are positioned while the third image camera 7C is disposed at the portion where the group of detectors 13 of the conventional TAB tester are positioned. The second and third image cameras 7B and 7C detect the presence and nonpresence of the TAB, presence and nonpresence of the IC chip, and presence and nonpresence of the marked hole with high accuracy by the image recognition. The image data taken by the second image camera 7B is stored in the control unit 10 as the second data which instructs the prosecution or non-prosecution of the measurement of the TAB when the latter is to be measured. The image data taken by the third image camera 7C is compared and collated with the image data taken by the second image camera 7B and also compared and collated with the punching instruction of the punch unit 6.

PREFERRED EMBODIMENT OF THE INVENTION

Figure 1:
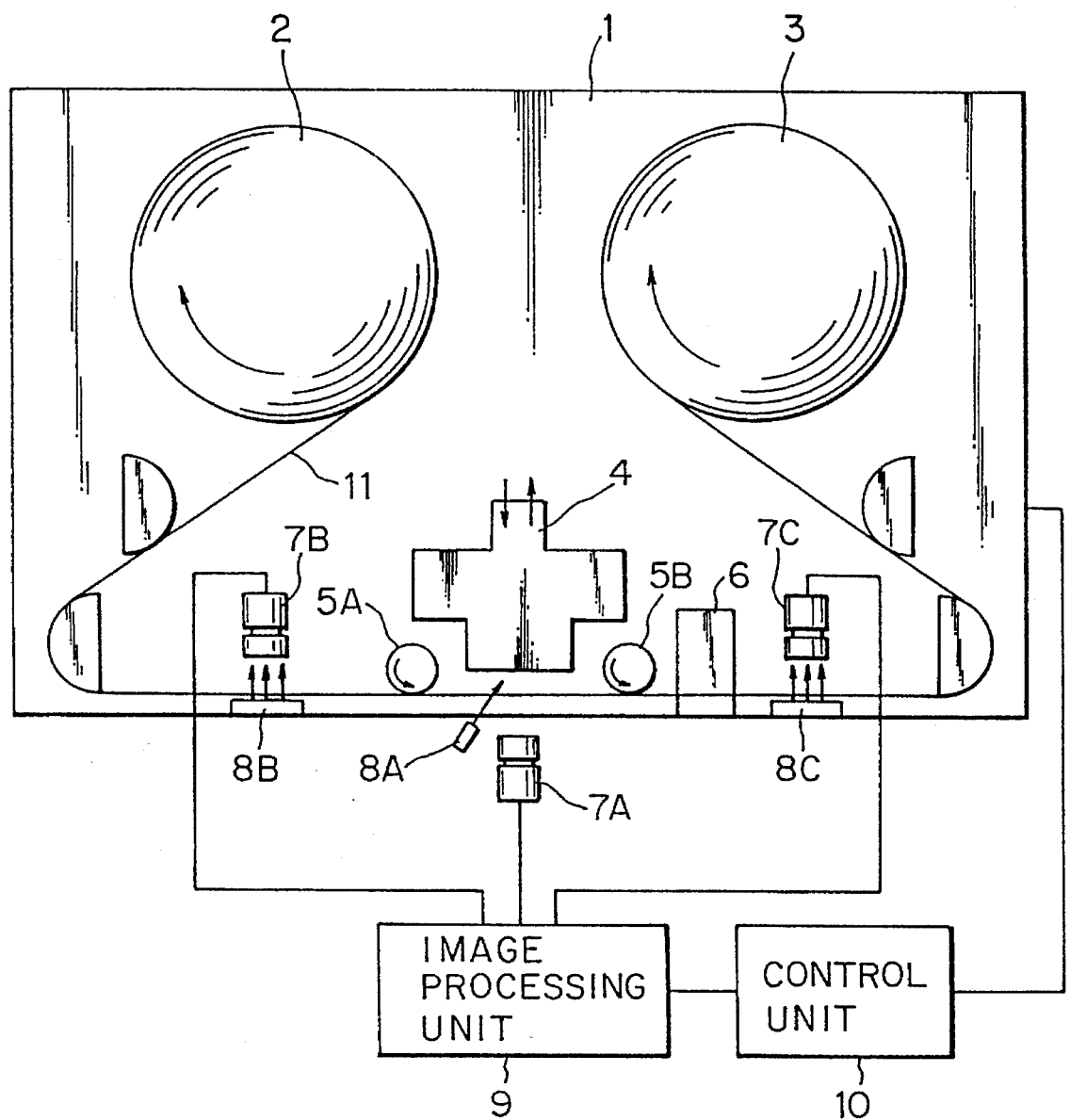
FIG. 1 shows an arrangement of a TAB tester according to a preferred embodiment of the invention.

A TAB tester according to a preferred embodiment of the present invention will be described with reference to FIGS. 1 to 3.

Figure 4:
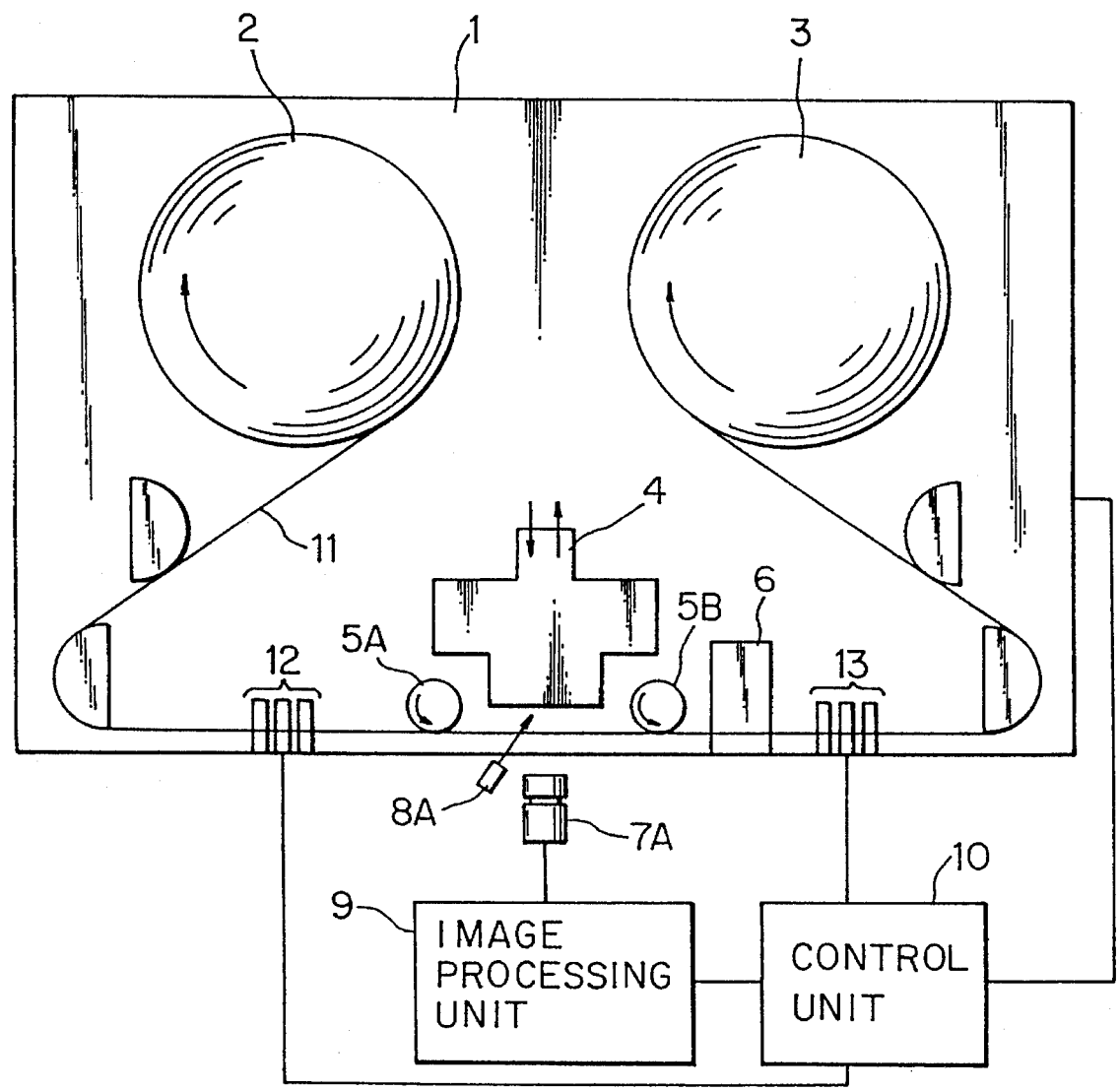
FIG. 4 shows an arrangement of a conventional TAB tester.
Figure 5:
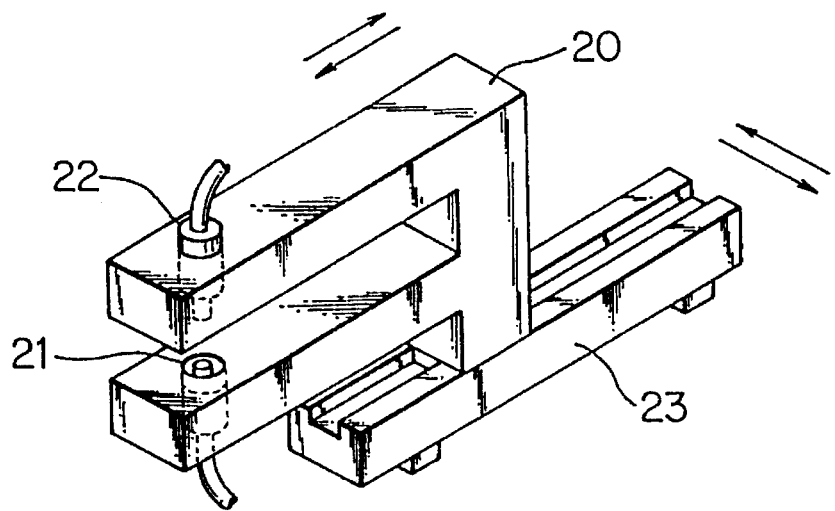
FIG. 5 shows an arrangement of a group of detectors 12 in FIG. 4.

The arrangement of the TAB tester of the present invention is substantially the same as that of the prior art TAB tester as illustrated in FIG. 4 excepting that image cameras 7B and 7C of the present invention are replaced by the group of detectors 12 and 13 of the conventional TAB tester and the former is connected to the image processing unit 9 although the latter is connected to the control unit 10 of the conventional TAB tester. Elements which are the same as those of the conventional TAB tester are denoted at the same numerals.

A second image taken by the second camera 7B is supplied to the image processing unit 9 where it is subjected to an image processing, namely, it is converted into a second image data. The second image data is supplied to and stored in the control unit 10. A third image taken by the third camera 7C is supplied to the image processing unit 9 where it is subjected to an image processing, namely, it is converted into a third image data. The third image data is supplied to and stored in the control unit 10.

Figure 2:
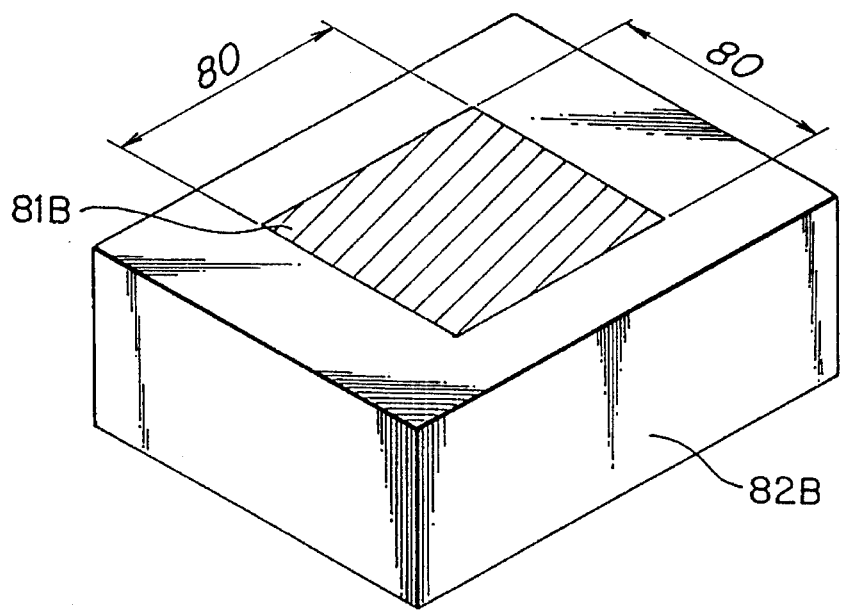
FIG. 2 is a view showing a light source 8B in detail.

FIG. 2 shows a light source 8B in detail. Since a light source 8C is the same as the light source 8B, the explanation of the light source 8C is omitted. Denoted at 81B is a light emitting surface and 82B is a light source box. The light emitting surface 81B has an area of about 80 mm ×80 mm which is slightly larger than the maximum size of the TAB to be measured by the TAB tester 1, namely, 70 mm ×76 mm. That is, the light sources 8B and 8C emit the light to the entire area of the TAB and the second and third image cameras 7B and 7C take images formed by transmitting light through the TAB. The light sources may be omitted if surroundings of use of the TAB tester are satisfied and the second and third image cameras 7B and 7C merely take images of the TAB.

Figure 3:
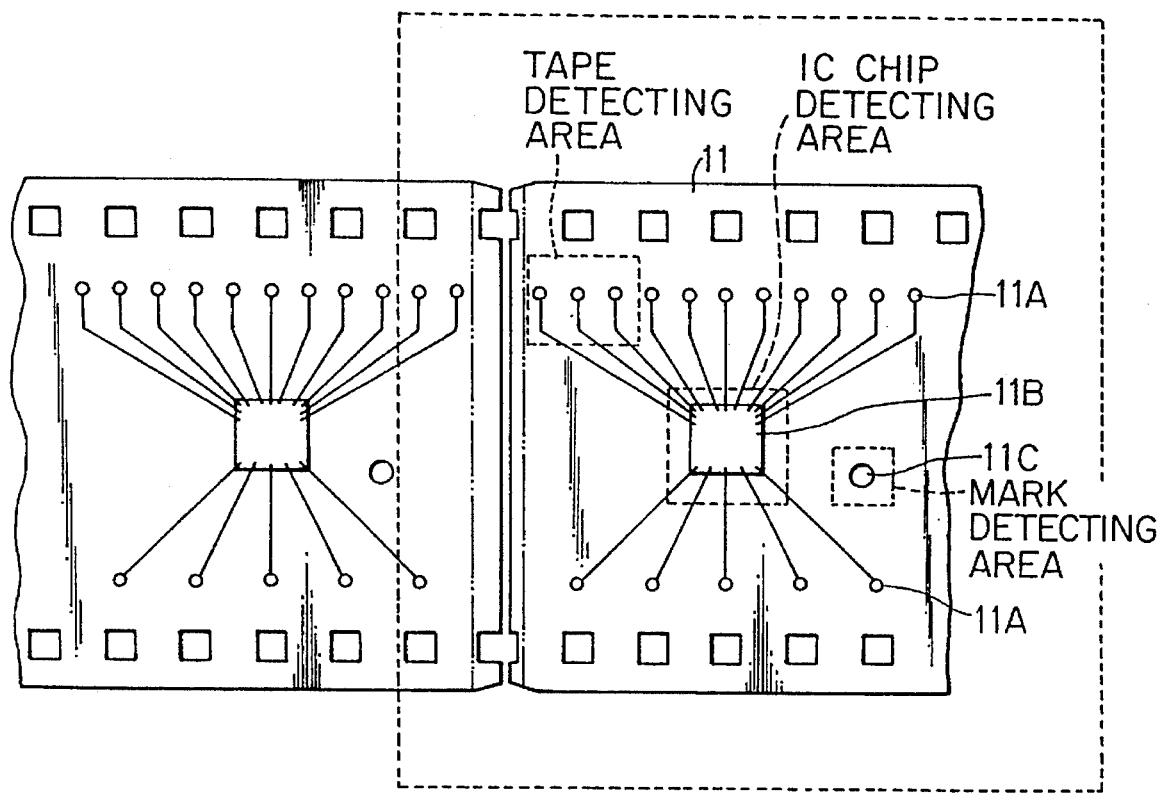
FIG. 3 is an image of a tape carrier 11 on a TV monitor.
Figure 6:
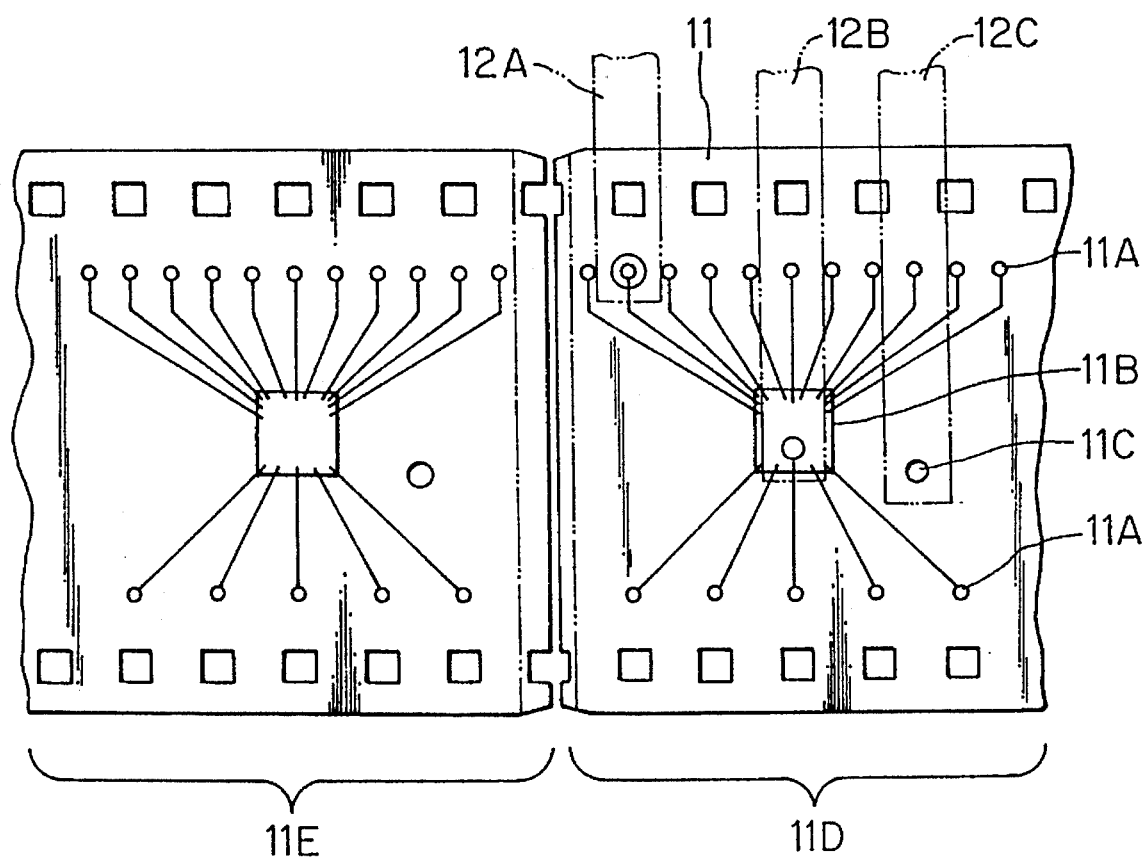
FIG. 6 shows the disposition of the group of detectors 12 on the tape carrier 11 in FIG. 4.

FIG. 3 shows an image on a TV monitor, not shown, when the image of the tape carrier 11 is taken by the second the image camera 7B. In FIG. 6, the group of detectors in the conventional TAB tester are mechanically moved but the image area is specified on the TV monitor.

In the same figure, a rectangular specified frame appears on the TV monitor and the specified frame is moved using a direction key, thereby specifying the image area. A given area of test pads 11A is surrounded by a specified frame and registered in the control unit 10 as a tape detecting area. Likewise, a given area of an IC chip 11B is surrounded by a specified frame and registered in the control unit 10 as an IC chip detecting area. In addition, the marked hole 11 is registered in the control unit 10 as a mark detecting area.

Successively, each area at the side of the third image camera 7C is registered in the control unit 10 but it is not necessary to be set individually since the data registered by the second image camera 7B can be applied to the each area at the side of the third image camera 7C. That is, the aforementioned three areas, namely, the tape detecting area, the IC chip detecting area and the mark detecting area can be moved collectively.

According to the present invention, it is possible to prevent the erroneous detection even if there are joints on the tape cartier since the marked hole of the TAB and the presence or nonpresence of the IC chip and the tape carrier can be detected by the image recognition on or before the measurement of the TAB. Furthermore, since the initial setting of the area where the TAB is detected can be performed on the TV monitor, the time involved in such setting can be reduced compared with the conventional TB tester. Still furthermore, if the setting is once registered, it is possible to use the registered data at the time when other lot members are measured, and hence the initial setting can be omitted at the next lot.

What is claimed is:

1. A TAB tester comprising:

a supply reel on which a tape carrier is mounted;

a pusher for pushing down the tape carrier downward for permitting the tape carrier to contact an IC tester so that the TAB can be subjected to an electric test by the IC tester;

a punch unit for punching the TAB of the tape carrier depending on the result of electric test by the IC tester to form an identification hole or punching an IC chip;

first and second sprockets and which are synchronously rotated for transferring the tape carrier;

a first image camera disposed under the pusher for taking a first image of the TAB which is transmitted by a light source and outputting the first image as a first image data;

a second image camera disposed upstream relative to the first sprocket, said second image camera taking a second image of the TAB and outputting the second image as a second image data;

a third image camera disposed downstream relative to the punch unit said third image camera taking a third image of the TAB and outputting the third image as a third image data;

an image processing unit for receiving first, second and third images from said first, second and third image cameras and subjecting the first, second and third images to image processings;

a control unit for controlling the position of the TAB based on the first processed image data when the TAB is measured, instructing execution and non-execution of the measurement of the TAB based on the second processed image data, and comparing and collating the third processed image data with the second processed image data and the punching result by the punch unit upon reception of the first, second and third processed image data from the image processing unit; and a winding reel for winding the tape carrier therein which was subjected to an electric test.

2. A TAB tester according to claim 1, further comprising a second light source disposed under said second image camera for emitting light toward an entire area of said TAB, a third light source disposed under said third image camera for emitting light toward an entire area of said TAB, and wherein said second image camera taking image of said TAB which is emitted by said second light source and outputting said second image as the second image data to said image processing unit while said third image camera taking image of said TAB which is emitted by said third light source and outputting said third image as the third image data to said image processing unit.

* * * * *

UNITED STATES PATENT AND TRADEMARK OFFICE
CERTIFICATE OF CORRECTION

PATENT NO. : 5 453 699
DATED : September 26, 1995
INVENTOR(S) : Hiroyuki MAKISHITA et al It is certified that error appears in the above-indentified patent and that said Letters Patent is hereby corrected as shown below:

Column 5, line 31; change "unit said" to
---unit, said---.

Signed and Sealed this

Sixteenth Day of January, 1996

Attest:

BRUCE LEHMAN

Attesting Officer

Commissioner of Patents and Trademarks